United States Patent
Popp et al.

(10) Patent No.: US 6,716,205 B2
(45) Date of Patent: Apr. 6, 2004

(54) PANT-LIKE ABSORBENT GARMENT HAVING TAILORED FLAP AND LEG ELASTIC

(75) Inventors: Robert Lee Popp, Hortonville, WI (US); Kathleen Irene Ratliff, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 289 days.

(21) Appl. No.: 09/750,446

(22) Filed: Dec. 28, 2000

(65) Prior Publication Data

US 2002/0087139 A1 Jul. 4, 2002

(51) Int. Cl.$^7$ ................................................. A61F 13/15
(52) U.S. Cl. ........................ 604/385.24; 604/385.23; 604/385.25; 604/385.3; 604/385.29; 604/385.28; 604/385.01; 604/378; 604/379
(58) Field of Search ................. 604/385.24, 385.25, 604/385.3, 385.29, 385.23, 385.01, 378, 379, 385.26, 385.27

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,601,717 A | 7/1986 | Blevins |
| 4,640,726 A | 2/1987 | Sallee et al. |
| 4,663,220 A | 5/1987 | Wisneski et al. |
| 4,681,579 A | 7/1987 | Toussant et al. |
| 4,883,549 A | 11/1989 | Frost et al. |
| 4,940,464 A | 7/1990 | Van Gompel et al. |
| 5,046,272 A | 9/1991 | Vogt et al. |
| 5,087,255 A | 2/1992 | Sims |
| 5,104,116 A | 4/1992 | Pohjola |
| 5,224,405 A | 7/1993 | Pohjola |
| 5,226,992 A | 7/1993 | Morman |
| 5,292,316 A | 3/1994 | Suzuki |
| 5,531,730 A | 7/1996 | Dreier |
| 6,049,024 A | 4/2000 | Thomas et al. |
| 6,217,563 B1 | 4/2001 | Van Gompel et al. |

FOREIGN PATENT DOCUMENTS

| | | | |
|---|---|---|---|
| EP | 0 217 032 | 4/1987 | |
| EP | 0 243 013 | 10/1987 | |
| EP | 0 648 482 A2 | 4/1995 | |
| GB | 2 284 538 A | 6/1995 | |
| WO | WO 94/12135 | 6/1994 | |
| WO | 95/16421 | 6/1995 | |
| WO | WO 96/14815 | 5/1996 | |
| WO | WO 9724096 A1 * | 7/1997 | ........... A61F/13/15 |
| WO | 98/16179 | 4/1998 | |

* cited by examiner

*Primary Examiner*—Weilun Lo
*Assistant Examiner*—Jacqueline F Stephens
(74) *Attorney, Agent, or Firm*—Pauley Petersen & Erickson

(57) ABSTRACT

A pant-like absorbent garment having a combined leg elastic and leak guard flap feature. A chassis of the absorbent garment includes an outer cover and a body side liner with at least one elastomeric member folded within the body side liner around each of two leg openings defined by the chassis to form a finished edge around each leg opening. The folded edge of the body side liner is then folded again to create a fully functional flap with the appearance of a leg elastic in the crotch area. The resulting absorbent garment has a three-dimensional leg elastic assembly that creates a bucket for containing body fluids, and furthermore, creates a tailored, soft, comfortable leg and side seal.

25 Claims, 7 Drawing Sheets

PANT-LIKE ABSORBENT GARMENT HAVING TAILORED FLAP AND LEG ELASTIC

FIELD OF THE INVENTION

This invention is directed to pant-like, personal care absorbent garments having fully functional leak guard flaps in combination with tailored edge leg elastics.

BACKGROUND OF THE INVENTION

Pant-like absorbent garments, such as adult incontinence wear, as well as infant and children's diapers, swim wear and training pants, typically include a pair of leg openings having an elastic portion around each leg opening. The elastic portions are intended to fit snugly around a wearer's legs to prevent leakage from the garment. However, these elastic portions alone are often inadequate defenses against leakage.

The use of leak guard flaps attached to the leg openings is known in the art. Leak guard flaps are intended to fit snugly against the wearer to effectively block most spillage of waste material from the leg openings. However, leak guard flaps in combination with the elastic portions around the leg openings results in a considerable amount of materials, which creates a bulky, sloppy look as well as considerable expense.

There is a need or desire for an absorbent garment having a low-cost leak guard flap and leg elastic feature.

There is a further need or desire for an absorbent garment having a leak guard flap and leg elastic feature resulting in a tailored appearance.

SUMMARY OF THE INVENTION

The present invention is directed to a pant-like absorbent garment, such as a training pant, swimsuit, diaper, incontinence garment or similar absorbent vehicle, having a leg elastic and a leak guard flap feature combined into one leg elastic assembly. More particularly, an elastomeric member can be rolled into the garment to create both a fully functional flap and a tailored edge leg elastic.

The leg elastic assembly can be formed by widening a liquid impermeable layer and a body side liner of the garment to form a tailored edge with an elastomeric member encompassed within the tailored edge. By widening the liquid impermeable layer and the body side liner, a liquid impermeable layer in the outer cover, leak guard flap cloth and leak guard flap elastic can all be eliminated from a conventional absorbent garment having separate leak guard flaps and leg elastics. By eliminating so many components from the conventional absorbent garment, the material cost of the garment can be noticeably reduced. The tailored edge encompassing an elastomeric member can then be rolled in so that the elastomeric member can form a side gasket with the functionality of a flap and the appearance of a leg elastic. The side panels can be added to the outer cover and can be sandwiched between the outer cover cloth and the liquid impermeable layer for added attachment strength.

The resulting product is an absorbent garment having a three-dimensional leg elastic assembly that creates a bucket for containing body fluids, and furthermore, creates a tailored, soft, comfortable leg and side seal.

With the foregoing in mind, it is a feature and advantage of the invention to provide an absorbent garment with a highly functional leg elastic assembly combining the attributes of a leg elastic and a leak guard flap.

It is another feature and advantage of the invention to provide an absorbent garment having a low-cost leg elastic assembly.

It is yet another feature and advantage of the invention to provide an absorbent garment having a tailored appearance around the leg openings.

DEFINITIONS

Figure 1:
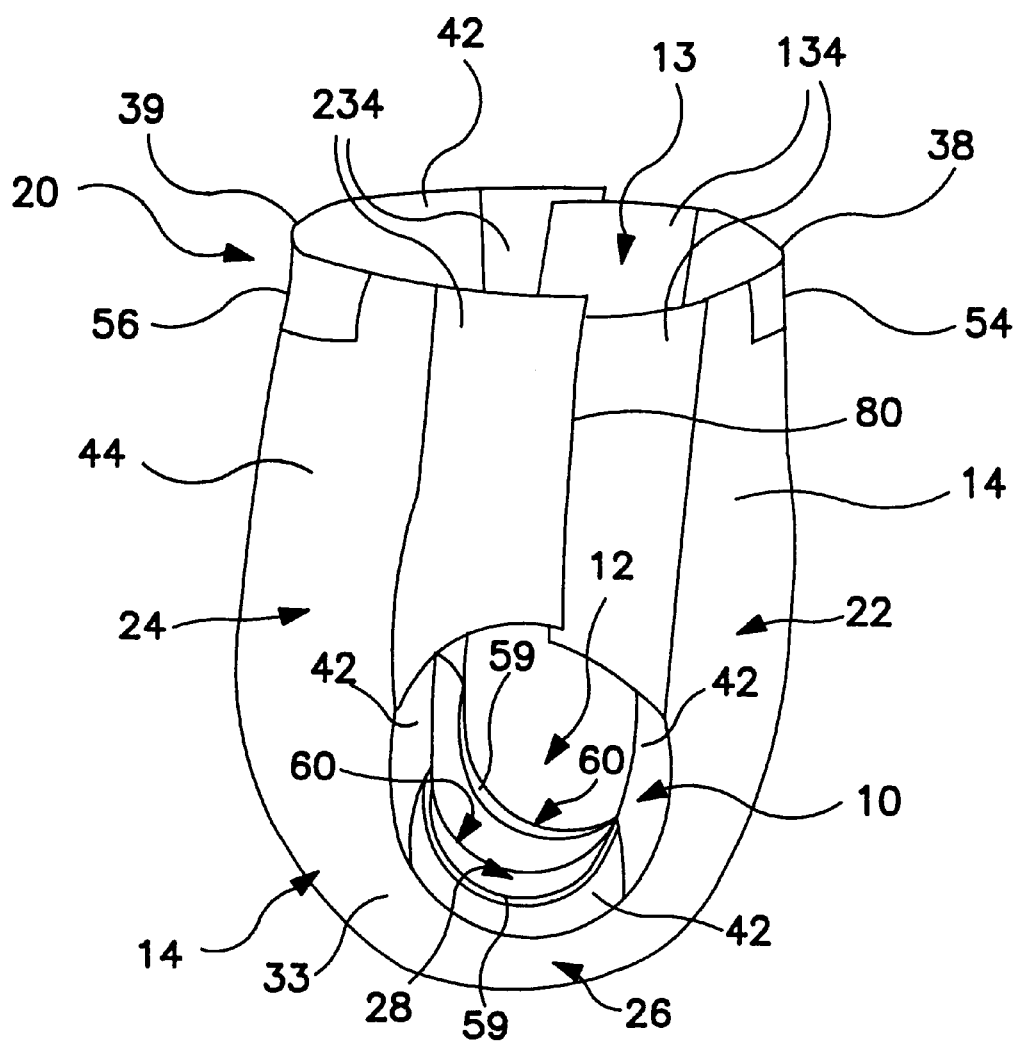
FIG. 1 is a side perspective view of an absorbent garment of the invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 40 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Leak guard flap" refers to one or more strips of material attached to or integral with a material defining a leg opening of a pant-like garment along one edge and having a piece of elastic attached along an opposite edge. The leak guard flap is intended to prevent lateral leakage of waste material from the garment through the leg openings.

"Leg elastic" refers to a strip of elastomeric material bonded along an edge of a leg opening of a pant-like garment. Leg elastics generally do not fit as snugly as leak guard flaps do.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact.

"Liquid-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid through the material.

Figure 2:
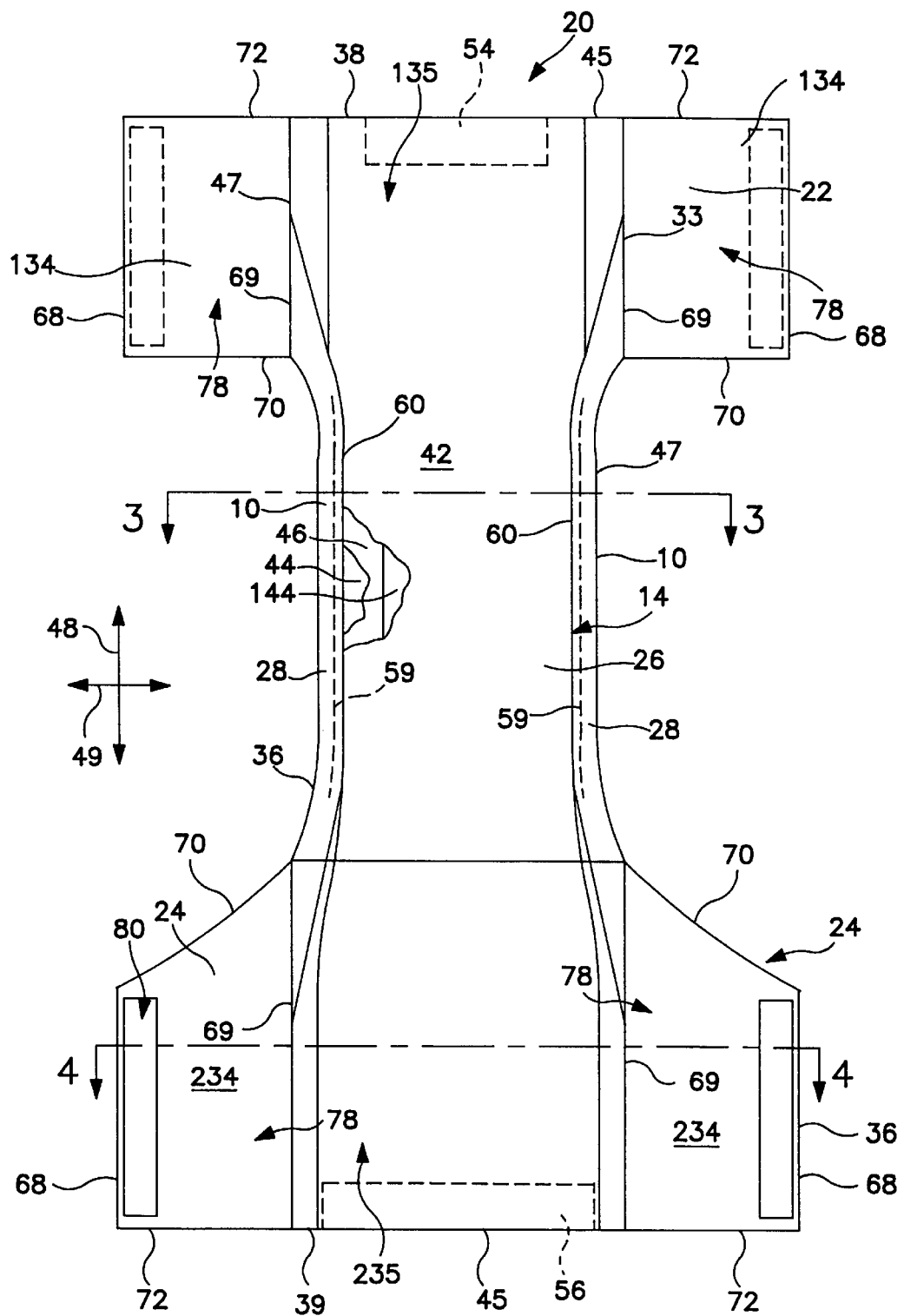
FIG. 2 is a plan view of the absorbent garment of FIG. 1 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 2. The longitudinal axis lies in the plane of the article and is generally parallel to a vertical plane that bisects a standing wearer into left and right body halves when the article is worn. The transverse axis lies in the plane of the article generally perpendicular to the longitudinal axis.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

These terms may be defined with additional language in the remaining portions of the specification.

DETAILED DESCRIPTION OF THE PRESENTLY PREFERRED EMBODIMENTS

The present invention is directed to a pant-like absorbent garment having the attributes of a leg elastic and a leak guard flap combined into a single leg elastic assembly. The leg elastic assembly is fully functional and provides a tailored appearance around leg openings in the garment. More particularly, the leg elastic assembly is formed by folding an edge of a body side liner around an elastomeric member and folding the body side liner onto itself along a transverse edge of the garment, as described in greater detail below.

The principles of the present invention can be incorporated into any suitable disposable absorbent garment. Examples of such suitable garments include diapers, training pants, incontinence products, other personal care or health care garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, an absorbent article, such as a training pant 20, is illustrated in a fastened condition. A main chassis 14 defines a pair of leg openings 12 and a waist opening 13. Leg elastic assemblies 10 are used around the leg openings 12 of the training pant 20 to act as both leg elastics and leak guard flaps. When the leg elastics and leak guard flaps are combined into the leg elastic assemblies 10, as in the present invention, the leg elastic assemblies 10 reduce or prevent leakage and, in addition, provide a tailored appearance around the leg openings 12. In the resulting garment 20, the three-dimensional leg elastic assemblies 10 create trough-like buckets 28 near the leg openings 12 for containing body fluids.

Referring to FIG. 2, the absorbent garment 20 of FIG. 1 is shown in a partially disassembled, stretched flat state, showing a surface which faces the wearer when the garment is worn. In addition to defining the leg openings 12 and the waist opening 13 (FIG. 1), the absorbent chassis 14 also defines a pair of transversely opposed side edges 36 and a pair of longitudinally opposed waist edges, which are designated front waist edge 38 and back waist edge 39. The chassis 14 also includes a somewhat rectangular composite structure 33, a pair of transversely opposed front side panels 134, and a pair of transversely opposed back side panels 234. The composite structure 33 and side panels 134 and 234 may be integrally formed, or, more suitably, may include two or more separate elements, as shown in FIG. 2.

The illustrated composite structure 33 includes an outer cover 44, a liquid impermeable layer 46 which is bonded to the outer cover 44 in a superposed relation, a body side liner 42 which is bonded to the liquid impermeable layer 46 in a superposed relation, and an absorbent assembly 144 which is located between the liquid impermeable layer 46 and the body side liner 42. The rectangular composite structure 33 has opposite linear end edges 45 that form portions of the front and back waist edges 38 and 39, and opposite linear, or curvilinear, side edges 47 that form portions of the side edges 36 of the absorbent chassis 14. Leg openings 12 (FIG. 1) are generally defined by portions of the transversely opposed side edges 36 and leg end edges 70. For reference, arrows 48 and 49 depicting the orientation of the longitudinal axis and the transverse axis, respectively, of the training pant 20 are illustrated in FIG. 2.

Figure 3:
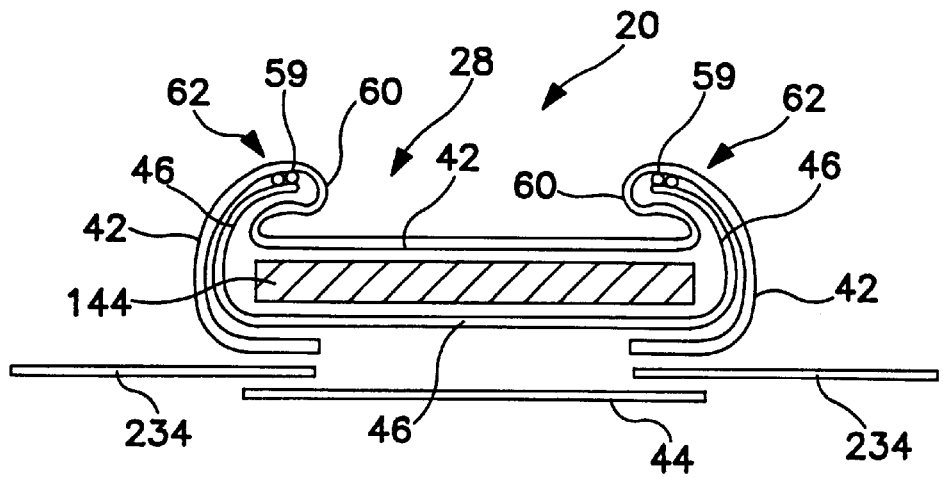
FIG. 3 is a cross-sectional view of the absorbent garment of FIG. 1, taken along line 4—4 in the back region.
Figure 4:
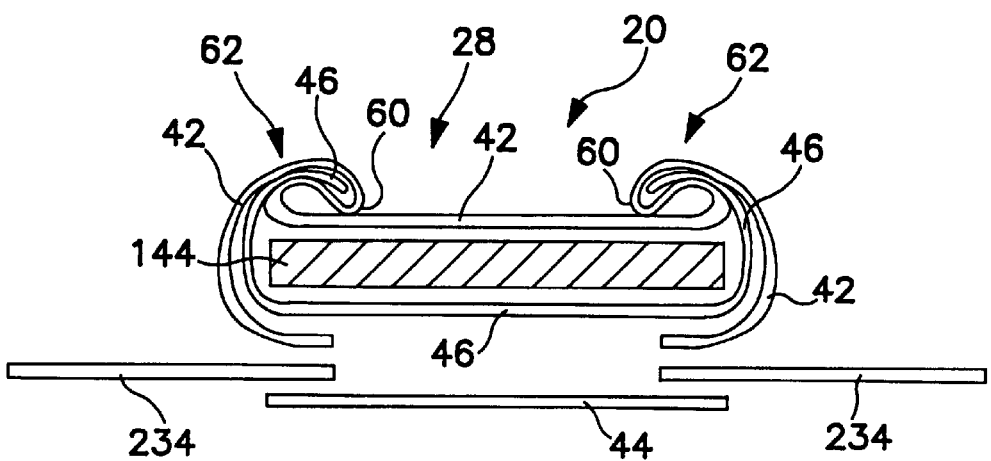
FIG. 4 is a cross-sectional view of the absorbent garment of FIG. 1, taken along line 4—4 in the back region.

As shown in FIG. 3, at least one elastomeric member 59 is located between the liquid impermeable layer 46 and the body side liner 42, and is bonded to the liquid impermeable layer 46 and/or the to body side liner 42, and the body side liner 42 is folded over the elastomeric member 59 and the liquid impermeable layer 46 to form a finished edge 60 along the linear side edges 47 in a crotch region 26 of the chassis 14. Alternatively, the body side liner 42 can be folded over the composite of the liner 42, the elastomeric member 59 and the liquid impermeable layer 46. The finished edge 60 of the body side liner 42 is folded over again along the linear side edges 47 to create a fully functional leak guard flap 62 with the appearance of a leg elastic in the crotch region 26, and the folded portion of the body side liner 42 is bonded either to itself or to the liquid impermeable layer 46 in a front region 22 and in a back region 24 of the chassis 14, as shown in FIG. 4. A bucket 28 is formed by the inner surfaces of the leak guard flaps 62 and the absorbent assembly 144. FIG. 3 shows a cross-sectional illustration through the crotch region 26 of the absorbent garment 20 shown in FIG. 2, and FIG. 4 shows a cross-sectional illustration through the back region 24 of the absorbent garment 20 shown in FIG. 2. The cross-section through the front region 22 is essentially the same as the cross-section through the back region 24.

The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front region 22 of the absorbent chassis 14 includes the transversely opposed front side panels 134 and a front center panel 135 (FIG. 2) positioned between and interconnecting the side panels 134, along with a front waist elastic member 54 and any other connected components. The back region 24 of the absorbent chassis 14 includes the transversely opposed back side panels 234 and a back center panel 235 (FIG. 2) positioned between and interconnecting the side panels 234, as well as a rear waist elastic member 56 and any other connected components. The waist edges 38 and 39 of the absorbent chassis 14 are configured to encircle the waist of the wearer when worn and provide the waist opening 13 which defines a waist perimeter dimension. Portions of the transversely opposed side edges 36 in the crotch region 26 and the leg end edges 70 of the side panels 134, 234 generally define the leg openings 12.

The side panels 134 and 234 are suitably bonded to the outer cover 44, with the side panels 134 and 234 either bonded between the outer cover 44 and the body side liner 42, or between the outer cover 44 and the liquid impermeable layer 46. By bonding the side panels 134 and 234 between two layers of the chassis 14, the side panels 134 and 234 are given added attachment strength.

Figure 5:
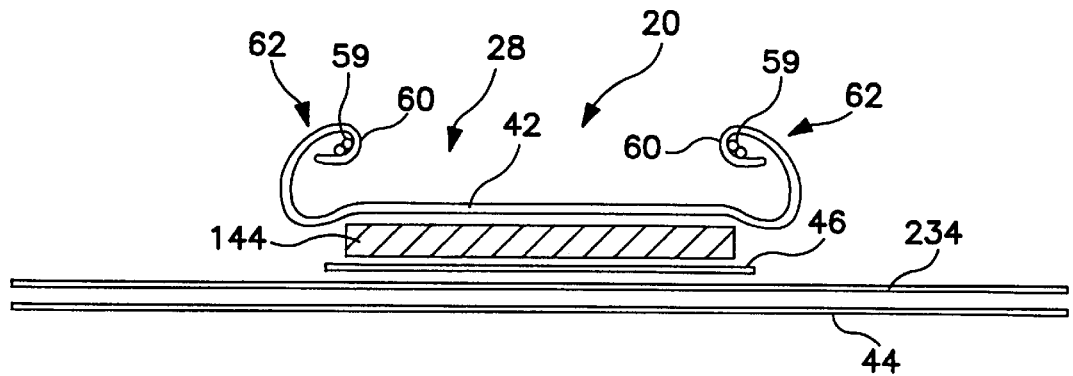
FIG. 5 is a cross-sectional view of another embodiment of the absorbent garment of the invention, taken along line 4—4 in the back region in FIG. 1.
Figure 6:
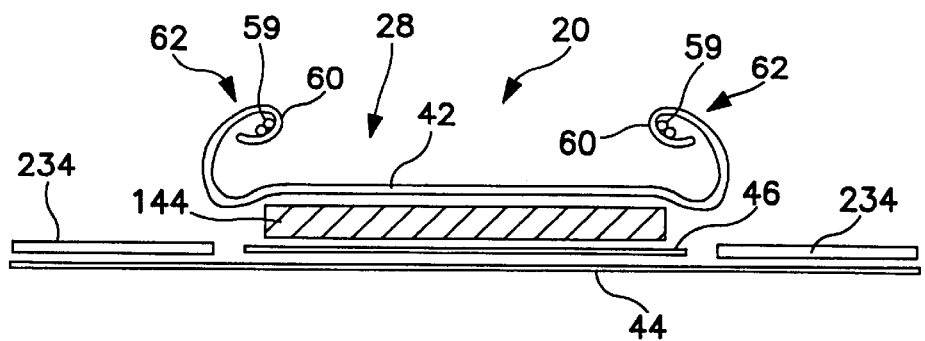
FIG. 6 is a cross-sectional view of another embodiment of the absorbent garment of the invention, taken along line 4—4 in the back region in FIG. 1.

In an alternative embodiment of the invention, the side panels 134, 234 can be an integral part of the outer cover 44. The side panels 134, 234 can extend all the way across the front and back regions of the garment on the outer cover 44 as shown in the back region 24 of a garment 20 in FIG. 5, or the side panels can be integrated with the outer cover 44 merely along the sides of the garment in the typical location of side panels as shown in the back region 24 of a garment in FIG. 6.

Figure 7:
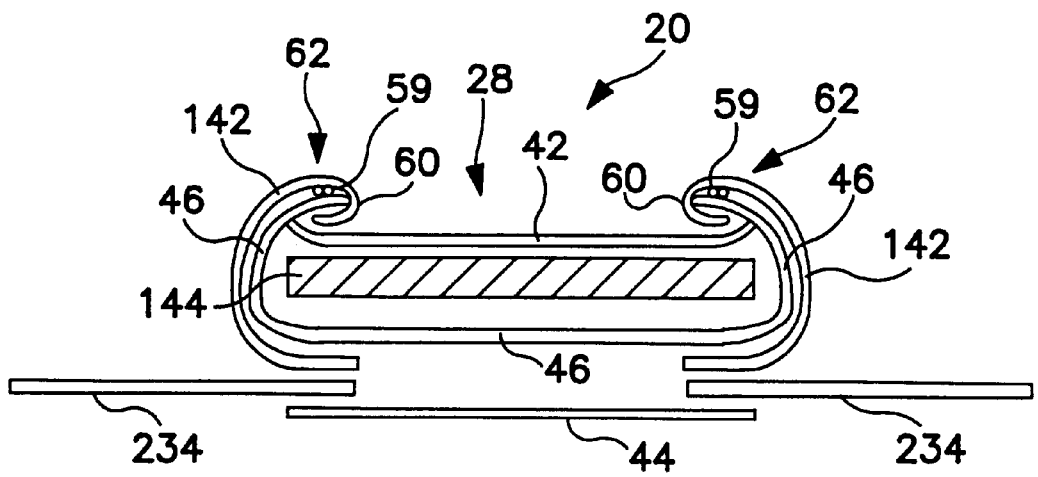
FIG. 7 is a cross-sectional view of another embodiment of the absorbent garment of the invention, taken along line 4—4 in the back region in FIG. 1.

In another alternative embodiment of the invention, the body side liner 42 is not wider than the liquid impermeable layer 46, but can be the same length or shorter. The body side liner 42 covers the absorbent assembly 144 and can be bonded to the liquid impermeable layer 46. An additional layer of nonwoven material 142, as shown in FIG. 7, can cover the liquid impermeable layer 46 on the outside edge to cover the liquid impermeable layer 46 that would lie against a wearer's leg. The body side liner 42 can cover all of the liquid impermeable layer 46 on the inside of the product or can be short such that some of the liquid impermeable layer 46 is exposed to the wearer's skin. Depending on the type of material used for the liquid impermeable layer 46, direct contact of the liquid impermeable layer 46 with a wearer's skin may or may not suitable. A cross-sectional illustration through a back region 24 of this embodiment is shown in FIG. 7.

Figure 8:
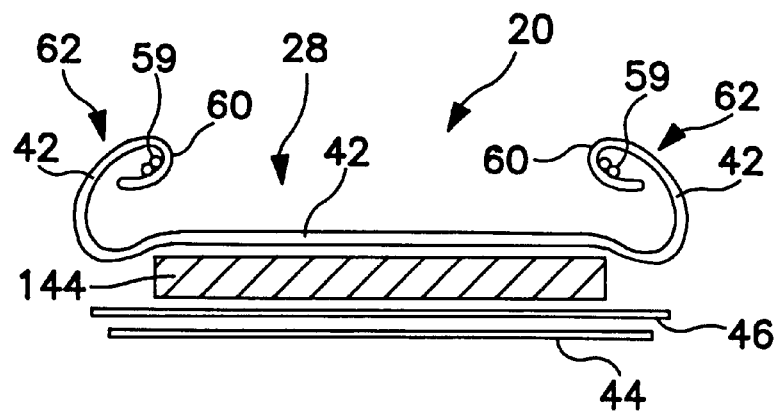
FIG. 8 is a cross-sectional view of another embodiment of the absorbent garment of the invention, taken along line 3—3 in the crotch region in FIG. 1.
Figure 9:
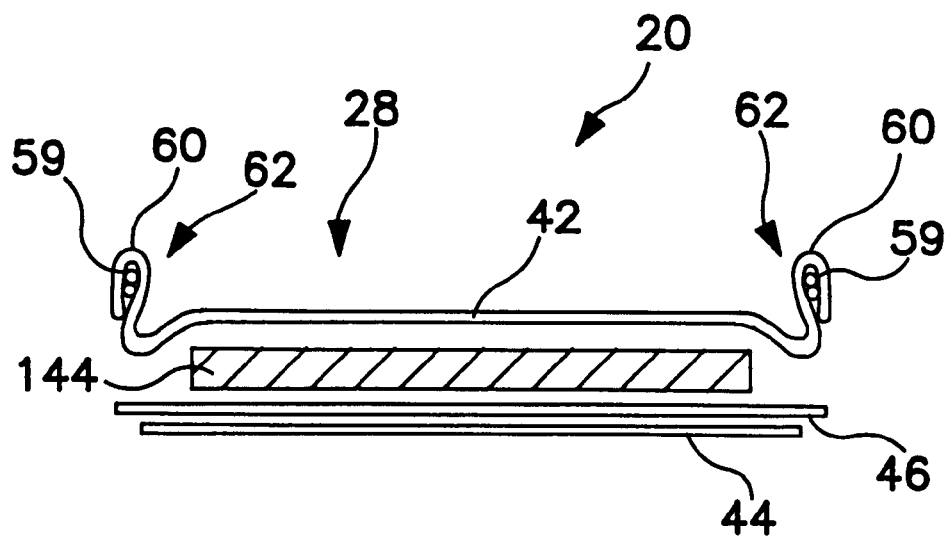
FIG. 9 is a cross-sectional view of another embodiment of the absorbent garment of the invention, taken along line 3—3 in the crotch region in FIG. 1.
Figure 10:
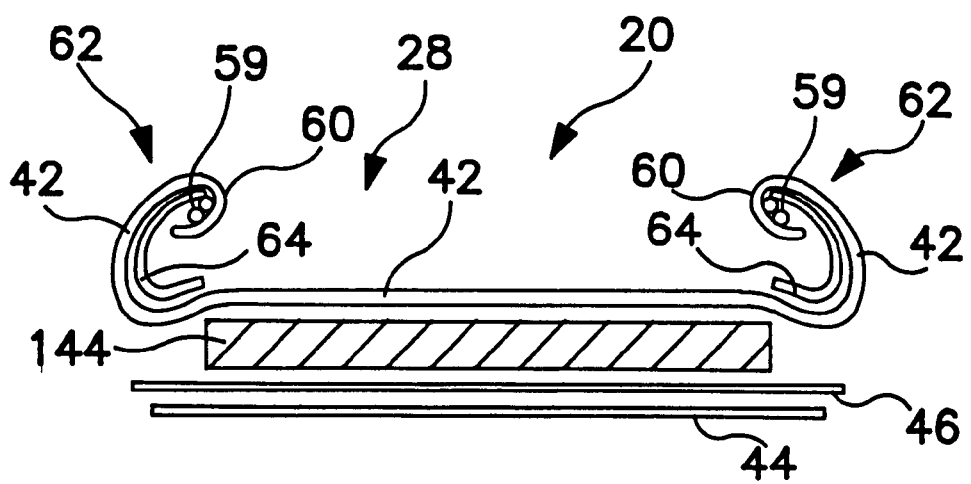
FIG. 10 is a cross-sectional view of another embodiment of the absorbent garment of the invention, taken along line 3—3 in the crotch region in FIG. 1.
Figure 11:
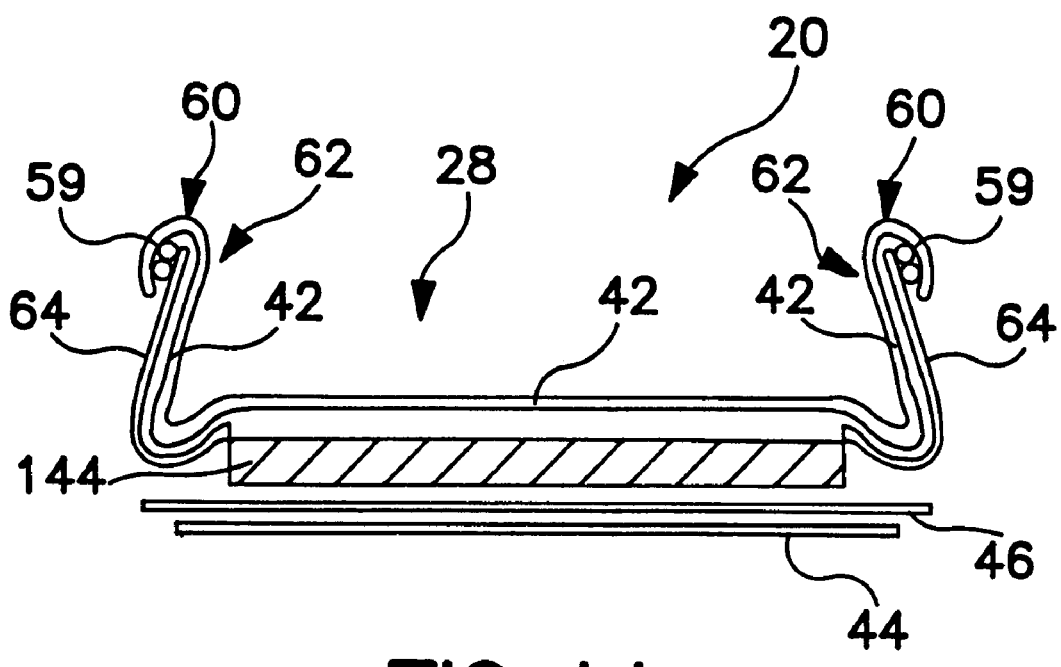
FIG. 11 is a cross-sectional view of another embodiment of the absorbent garment of the invention, taken along line 3—3 in the crotch region in FIG. 1.

In yet another alternative embodiment of the invention, the side panels 134 and 234 can be bonded between the body side liner 42 and the liquid impermeable layer 46. In this embodiment, the elastomeric members 59 are folded within the body side liner 42 rather than between the body side liner 42 and the liquid impermeable layer 46. In this embodiment, the elastomeric members 59 can either be folded inside the body side liner 42 with the body side liner 42 folded away from the side panels 134 and 234, as shown in FIG. 8, or with the body side liner 42 folded toward the side panels 134 and 234, as shown in FIG. 9. The body side liner 42 is normally a liquid permeable layer, however, in this embodiment the body side liner 42 is desirably liquid permeable in the center of the product over the absorbent layer 144 and liquid impermeable in the flap area. This zone treatment can be accomplished by using a liquid impermeable body side liner 42 and treating the liner 42 over the absorbent assembly 144 by punching holes in the liner 42 or perforating the liner 42 to make it liquid permeable over the absorbent assembly 144. Another alternative would be to use a liquid permeable body side liner 42 and to treat the outside area by the flaps 62 or trough area to be liquid impermeable by, for example, coating the liner 42 in these areas with water repellant materials, such as coating it with polyethylene, polypropylene, coating the liner 42 with a meltblown layer or covering the liner 42 in this area with silicone to repel urine. Such zone treatment could also be accomplished by laminating an additional liquid impermeable layer 64 over the flap area 62 to effectively zone the liner 42 to be liquid impermeable over the flap area 62, as illustrated in FIGS. 10 and 11. There are many ways well-known in the art to zone treat a liquid permeable material to be selectively liquid impermeable.

The liquid permeable body side liner 42 is illustrated as overlying the outer cover 44, the liquid impermeable layer 46 and the absorbent assembly 144 (FIG. 2). Suitably, the width of the body side liner 42 in the transverse direction 49 is wider than the outer cover 44, but the length of the body side liner 42 in the longitudinal direction 48 may be the same as the length of the outer cover 44. The body side liner 42 is desirably compliant, soft feeling, and non-irritating to the child's skin. Further, the body side liner 42 can be less hydrophilic than the absorbent assembly 144, to present a relatively dry surface to the wearer and permit liquid to readily penetrate through its thickness.

The leak guard flaps 62 can be, but do not necessarily have to be, attached to the body side liner 42 in the front region 22 and in the back region 24 of the garment 20. The flaps 62 can be tacked down at a single point in each region 22, 24, or at multiple points, or across the entire widths of the flaps 62. Bonding of the leak guard flaps 62 to the body side liner 42 can be carried out by any suitable means, including ultrasonic bonding, or a variety of other techniques including adhesive bonding, thermal bonding, stitch bonding or other conventional techniques.

The absorbent assembly 144 is positioned between the body side liner 42 and the liquid impermeable layer 46, which components, along with the outer cover 44, can be joined together by any suitable means, such as adhesives, as is well known in the art. The absorbent assembly 144 can be any structure which is generally compressible, conformable, non-irritating to the child's skin, and capable of absorbing and retaining liquids and certain body wastes. The absorbent assembly 144 can be manufactured in a wide variety of sizes and shapes, and from wide variety of liquid absorbent materials commonly used in the art. For example, the absorbent assembly 144 can suitably include a matrix of hydrophilic fibers, such as a web of cellulosic fluff, mixed with particles of a high-absorbency material commonly known as superabsorbent material. In a particular embodiment, the absorbent assembly 144 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 144 to better contain and absorb body exudates. The concentration of the superabsorbent particles can also vary through the thickness of the absorbent assembly 144. Alternatively, the absorbent assembly 144 can include a laminate of fibrous webs and superabsorbent material or other suitable means of maintaining a superabsorbent material in a localized area. Another type of absorbent material suitable for the absorbent assembly 144 is coform, which is a blend of staple length and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the co-form to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 144 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 144 in an amount of from about 0 to about 90 weight percent based on total weight of the absorbent assembly. The absorbent assembly 144 suitably has a density within the range of about 0.10 to about 0.35 grams per cubic centimeter. The absorbent assembly 144 may or may not be wrapped or encompassed by a suitable tissue wrap that maintains the integrity and/or shape of the absorbent assembly.

The absorbent chassis 14 can also incorporate other materials that are designed primarily to receive, temporarily store, and/or transport liquid along the mutually facing surface with the absorbent assembly 144, thereby maximizing the absorbent capacity of the absorbent assembly. One suitable material is referred to as a surge layer (not shown)

and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Va., U.S.A.

A wide variety of elastic materials may be used for the elastic members 59 of the leg elastic assemblies. As is well known to those skilled in the art, suitable elastic materials include sheets, strands or ribbons of natural rubber, synthetic rubber, or thermoplastic elastomeric polymers, such as extruded polyurethane film. One particular type of suitable elastic material is a plurality of dry-spun coalesced multifilament spandex elastomeric threads sold under the trade name LYCRA® and available from E.I. DuPont de Nemours and Company, Wilmington, Del., U.S.A. Each of the elastomeric members 59 preferably has elongation of 25–350%, more preferably about 30–260%, most preferably about 35–200%.

The elastomeric members 59 can be stretched and adhered to the body side liner 42, adhered to the gathered body side liner 42, or adhered to the body side liner 42 and then elasticized or shrunk, for example with the application of heat; such that elastic constrictive forces are imparted to the substrate. One method of stretching elastic materials and adhering them to a substrate is taught in U.S. Pat. No. 4,883,549 issued Nov. 28, 1989 to Frost, et al., and is incorporated herein by reference. Heat shrinkable elastic is taught in U.S. Pat. No. 4,640,726 issued Feb. 3, 1987 to Sallee, et. al., and is incorporated herein by reference. In one particular embodiment, for example, the leg elastic assemblies 10 include a stretch-bonded laminate (SBL), as described in greater detail below.

Bonding of the elastomeric members 59 to the body side liner 42 and/or to the liquid impermeable layer 46 can be carried out by any suitable means, including ultrasonic bonding, or a variety of other techniques including adhesive bonding, thermal bonding, stitch bonding or other conventional techniques. Suitable adhesives include spray adhesives, hot melt adhesives, self-adhering elastomeric materials and the like.

The outer cover 44 includes a material that can be elastic, stretchable or nonstretchable. The outer cover 44 can be a single layer of liquid impermeable material, but desirably includes a multi-layered laminate structure in which at least one of the layers is the liquid impermeable layer 46. For instance, the outer cover 44 and the liquid impermeable layer 46 can be at least partially joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer cover 44 can be any suitable material and desirably one that provides a generally cloth-like texture. One example of such a material is a 20 gsm (grams per square meter) spunbond polypropylene nonwoven web. The outer cover 44 may also be made of those materials of which the liquid permeable body side liner 42 is made. While it is not a necessity for the outer cover 44 to be liquid permeable, it is desired that it provides a relatively cloth-like texture to the wearer.

The liquid impermeable layer 46 can be both liquid and vapor impermeable, or can be liquid impermeable and vapor permeable. The liquid impermeable layer is desirably manufactured from a thin plastic film, although other flexible liquid impermeable materials may also be used. The liquid impermeable layer 46 prevents waste material from wetting articles, such as bedsheets and clothing, as well as the wearer and caregiver. A suitable liquid impermeable film for use as a liquid impermeable layer 46 is a 0.02 millimeter polyethylene film commercially available from Huntsman Packaging of Newport News, Va., U.S.A. The liquid impermeable layer 46 can be printed upon such that any graphics or other printed matter can be visible through the outer cover.

As mentioned, the liquid impermeable material can permit vapors to escape from the interior of the absorbent article, while still preventing liquids from passing through the liquid impermeable layer 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner 42 can be composed of a meltblown or spunbonded web of polyolefin fibers. The body side liner 42 can also be a bonded-carded web composed of natural and/or synthetic fibers. The body side liner 42 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 42 or can be selectively applied to particular sections of the body side liner 42. By zone treating the body side liner 42 with surfactant in the medial section along the longitudinal centerline, thereby creating zones of greater liquid permeability between the two leg openings 12 compared to zones of lesser liquid permeability adjacent the first and second leg openings 12, for example, the body side liner 42 can serve as both a good flap material and a good liner material. Additional methods of zone treating the body side liner 42 include punching holes, or the like, in a liquid-impermeable material in the medial section, or making the outer edges over the flaps 62 impermeable by adding an additional layer, such as a polyethylene, or coating the nonwoven web with a material, or spraying the nonwoven web with a moisture repellant.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 44 and body side liner 42 can include elastomeric materials, alternatively, in some embodiments, the composite structure can be generally inelastic, where the outer cover 44, the body side liner 42 and the absorbent assembly 144 can include materials that are generally not elastomeric.

As noted previously, the illustrated training pant 20 can have front and back side panels 134 and 234 disposed on each side of the absorbent chassis 14 (FIGS. 1 and 2). These transversely opposed front side panels 134 and transversely opposed back side panels 234 can be permanently bonded to the composite structure 33 of the absorbent chassis 14 and can be releasably attached to one another by a fastening system 80. Alternatively, instead of refastenable seams, the absorbent garment 20 of the invention can have bonded side seams. More particularly, as shown best in FIG. 2, the front side panels 134 can be permanently bonded to and extend transversely beyond the linear side edges 47 of the composite structure 33 along attachment lines 69, and the back side panels 234 can be permanently bonded to and extend transversely beyond the linear side edges 47 of the composite structure along attachment lines 69. The side panels 134 and 234 may be attached using attachment means known to those skilled in the art such as adhesive, thermal or ultrasonic bonding. The side panels 134 and 234 can also be formed as a portion of a component of the composite structure 33, such as the outer cover 44 or the body side liner 42.

Each of the side panels 134 and 234 can include one or more individual, distinct pieces of material. In particular embodiments, for example, each side panel 134 and 234 can include first and second side panel portions that are joined at a seam (not shown), with at least one of the portions including an elastomeric material. Still alternatively, each individual side panel 134 and 234 can include a single piece of material which is folded over upon itself along an intermediate fold line (not shown). As a further alternative, the front and back side panels 134, 234 can be combined into a single side panel (not shown) on each side of the garment 20, with the single side panel attached directly to the chassis 14.

The side panels 134 and 234 desirably include an elastic material capable of stretching in a direction generally parallel to the transverse axis 49 of the training pant 20. In particular embodiments, the front and back side panels 134 and 234 may each include an interior portion 78 disposed between a distal edge 68 and a respective front or back center panel 135 or 235. In the illustrated embodiment in FIG. 2, the interior portions 78 are disposed between the distal edges 68 and the side edges 47 of the rectangular composite structure 33. The elastic material of the side panels 134 can be disposed in the interior portions 78 to render the side panels elastomeric in a direction generally parallel to the transverse axis 49. Most desirably, each side panel 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 69 to the distal edge 68 and a width of about 2 centimeters, are all elastomeric. Alternatively, the side panels 134, 234 can be an integral part of the garment 20 by using a wider outer cover 44 and incorporating elastic properties into the outer cover 44. The leg openings 12 can be formed by cutting along the leg end edge 70. Elastic can be added to the outer cover 44 in both the front and back regions 22, 24 of the garment 20 and can extend all the way across the outer cover 44 in the transverse direction, or can extend partially across the outer cover 44 between the absorbent assembly 144 and the distal edges 68 or anywhere in between.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 44 or body side liner 42, or stretchable but inelastic materials.

As described herein, the various components of the training pant 20 can be integrally assembled together employing various types of suitable attachment means, such as adhesive, sonic and thermal bonds or combinations thereof. The resulting product is an absorbent garment 20 having a three-dimensional leg elastic assembly 10 that creates a bucket 28 for containing body fluids around each leg opening, and furthermore, creates a tailored, soft comfortable leg and side seal about the leg openings.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A pant-like garment, comprising:

a chassis including an outer cover and a body side liner, and defining a waist opening and first and second leg openings;

a liquid impermeable layer adjacent the outer cover and situated between the outer cover and the body side liner; and at least one elastomeric member folded within and bonded to the body side liner around at least a portion of each of the first and second leg openings thereby forming leak guard flap regions along transverse edges of the body side liner, wherein the body side liner is folded over each of the at least one elastomeric members and is bonded onto itself in a front region and in a back region of the chassis, and the body side liner is bonded to the liquid impermeable layer along inward edges of the leak guard flap regions in at least a portion of a crotch region of the chassis, and distal edges of the leak guard flap regions are not bonded to the liquid impermeable layer in at least a portion of the crotch region of the garment.

2. The pant-like garment of claim 1, wherein the at least one elastomeric member is situated between the liquid impermeable layer and the body side liner around each of the first and second leg openings in the front and back regions of the chassis.

3. The pant-like garment of claim 1, further comprising at least two pairs of side panels bonded between the outer cover and the liquid impermeable layer.

4. The pant-like garment of claim 1, further comprising at least two pairs of side panels integrated with the outer cover, wherein the at least two pairs of side panels at least partially define the first and second leg openings.

5. The pant-like garment of claim 1, wherein the liquid impermeable layer comprises a print-receiving surface such that any printing on the liquid impermeable layer is visible through a nonwoven web layer of the outer cover.

6. The pant-like garment of claim 1, further comprising an absorbent layer between the outer cover and the body side liner.

7. The pant like garment of claim 6, wherein each of the at least one elastomeric members is folded within the body side liner a set distance from the absorbent layer.

8. The pant-like garment of claim 1, wherein the body side liner is zone-treated to create zones of greater liquid permeability between the first and second leg openings compared to zones of lesser liquid permeability adjacent the first and second leg openings.

9. The pant-like garment of claim 1, comprising training pants.

10. The pant-like garment of claim 1, comprising a diaper.

11. The pant-like garment of claim 1, comprising swim wear.

12. The pant-like garment of claim 1, comprising an incontinence garment.

13. An absorbent garment, comprising:
a chassis including an outer cover and a body side liner, and defining a waist opening and first and second leg openings;
a liquid impermeable layer situated between the outer cover and the body side liner, wherein the liquid impermeable layer, the outer cover and the body side liner each include two transverse edges and two longitudinal edges;
a pair of corresponding side panels along each transverse edge of the outer cover; and
at least one elastomeric member situated between the liquid impermeable layer and the body side liner around each of the first and second leg openings thereby forming leak guard flap regions along transverse edges of the body side liner, wherein each of the transverse edges of the body side liner is folded over at least one of the elastomeric members and is bonded onto an inward portion of the body side liner in a front region and in a back region of the chassis, and the body side liner is bonded to the liquid impermeable layer along inward edges of the leak guard flap regions in at least a portion of a crotch region of the chassis, and the transverse edges of the body side liner are not bonded to the liquid impermeable layer in at least a portion of the crotch region of the chassis.

14. The absorbent garment of claim 13, wherein the liquid impermeable layer comprises a print-receiving surface such that any printing on the liquid impermeable layer is visible through a nonwoven web layer of the outer cover.

15. The absorbent garment of claim 13, further comprising an absorbent layer between the liquid impermeable layer and the body side liner.

16. The absorbent garment of claim 15, wherein each of the at least one elastomeric members is folded within the body side liner a set distance from the absorbent layer.

17. The absorbent garment of claim 13, wherein each of the transverse edges of the body side liner is folded over at least one of the elastomeric members, and is folded over and bonded onto itself.

18. The absorbent garment of claim 13, comprising the pair of corresponding side panels attached along each transverse edge of the outer cover between the outer cover and the liquid impermeable layer.

19. The absorbent garment of claim 13, wherein the body side liner is zone-treated to create zones of greater liquid permeability between the first and second leg openings compared to zones of lesser liquid permeability adjacent the first and second leg openings.

20. An absorbent garment, comprising:
a chassis including an outer cover and a body side liner, and defining a waist opening and first and second leg openings;
a liquid impermeable layer situated between the outer cover and the body side liner;
an absorbent layer situated between the liquid impermeable layer and the body side liner;
at least one elastomeric member situated between the liquid impermeable layer and the body side liner around each of the first and second leg openings thereby forming leak guard flap regions along transverse edges of the body side liner, wherein the body side liner is folded over each of the at least one elastomeric members and is bonded onto itself a set distance from the absorbent layer in a front region and in a back region of the chassis, and the body side liner is bonded to the liquid impermeable layer along inward edges of the leak guard flap regions in at least a portion of a crotch region of the chassis, and distal edges of the leak guard flap regions are not bonded to the liquid impermeable layer in at least a portion of the crotch region of the chassis.

21. The absorbent garment of claim 20, further comprising at least two pairs of side panels bonded between the outer cover and the liquid impermeable layer.

22. The absorbent garment of claim 20, further comprising at least two pairs of side panels integrated with the outer cover, wherein the at least two pairs of side panels at least partially define the first and second leg openings.

23. The absorbent garment of claim 20, wherein the liquid impermeable layer comprises a print-receiving surface such that any printing on the liquid impermeable layer is visible through a nonwoven web layer of the outer cover.

24. The absorbent garment of claim 20 wherein each of the at least one elastomeric members is folded within the body side liner a set distance from the absorbent layer.

25. The absorbent garment of claim 20, wherein the body side liner is zone-treated to create zones of greater liquid permeability between the first and second leg openings compared to zones of lesser liquid permeability adjacent the first and second leg openings.

* * * * *